United States Patent
Bastian

(10) Patent No.: US 7,632,279 B2
(45) Date of Patent: Dec. 15, 2009

(54) PATELLA RESECTION CLAMP

(75) Inventor: Adam Bastian, Chester, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1037 days.

(21) Appl. No.: 11/022,738

(22) Filed: Dec. 27, 2004

(65) Prior Publication Data

US 2006/0142777 A1   Jun. 29, 2006

(51) Int. Cl.
  A61B 17/58   (2006.01)
  A61B 17/60   (2006.01)
  A61F 2/00    (2006.01)
(52) U.S. Cl. ........................... 606/88; 606/105
(58) Field of Classification Search .......... 606/86, 606/86 R, 87, 88, 105; 81/328, 420
See application file for complete search history.

(56) References Cited

U.S. PATENT DOCUMENTS

| | | | |
|---|---|---|---|
| 4,663,862 A | 5/1987 | Gorissen | |
| 4,706,660 A | 11/1987 | Petersen | |
| 4,721,104 A | 1/1988 | Kaufman et al. | |
| 4,759,350 A | 7/1988 | Dunn | |
| 5,021,055 A | 6/1991 | Burkinshaw | |
| 5,108,401 A | 4/1992 | Insall | |
| 5,129,907 A | 7/1992 | Heldreth et al. | |
| 5,147,365 A * | 9/1992 | Whitlock et al. | 606/88 |
| 5,222,955 A | 6/1993 | Mikhail | |
| 5,284,482 A | 2/1994 | Mikhail | |
| 5,417,695 A | 5/1995 | Axelson, Jr. | |
| 5,441,884 A | 8/1995 | Baum | |
| 5,486,177 A | 1/1996 | Mumme et al. | |
| 5,542,947 A * | 8/1996 | Treacy | 606/88 |
| 5,575,793 A | 11/1996 | Carls et al. | |
| 5,716,362 A | 2/1998 | Treacy | |
| 5,941,884 A | 8/1999 | Corvelli et al. | |
| 6,010,509 A | 1/2000 | Delgado et al. | |
| 6,159,246 A | 12/2000 | Mendes | |
| 6,174,314 B1 | 1/2001 | Waddell | |

(Continued)

OTHER PUBLICATIONS

Biomet Catalog; Simple Instruments—Surgical Technique for the Knee.

*Primary Examiner*—Thomas C Barrett
*Assistant Examiner*—Andrew Yang
(74) *Attorney, Agent, or Firm*—Lerner, David, Littenberg, Krumholz & Mentlik, LLP

(57) ABSTRACT

A patella resection clamp for use in resecting a patella has a first elongated handle portion and a second elongated handle portion. Each of the portions having first and second ends. The two handle portions are pivotally connected at a pivot point intermediate the first and second ends for rotation about a pivot axis. The second end of each of the elongated handle portions include a jaw with the jaw of the first and second handle portions spaced from the second end of the elongated portions in a direction parallel to the pivot axis. The jaws are spaced to form an opening therebetween for receiving the proximal and distal edges of the patella. The jaw portions including a saw blade guide surface or slot open to at least one of the first or second ends of each of said jaw portions. The guide surface or slot is for receiving a saw blade extending under (posteriorly) the handle portions and in a direction perpendicular to the pivot axis and perpendicular to the gripping direction of the jaws.

32 Claims, 13 Drawing Sheets

U.S. PATENT DOCUMENTS 6,277,121 B1 8/2001 Burkinshaw et al.
6,602,258 B1 8/2003 Katz
2003/0163137 A1 8/2003 Smucker et al.
2003/0171757 A1 9/2003 Coon

* cited by examiner

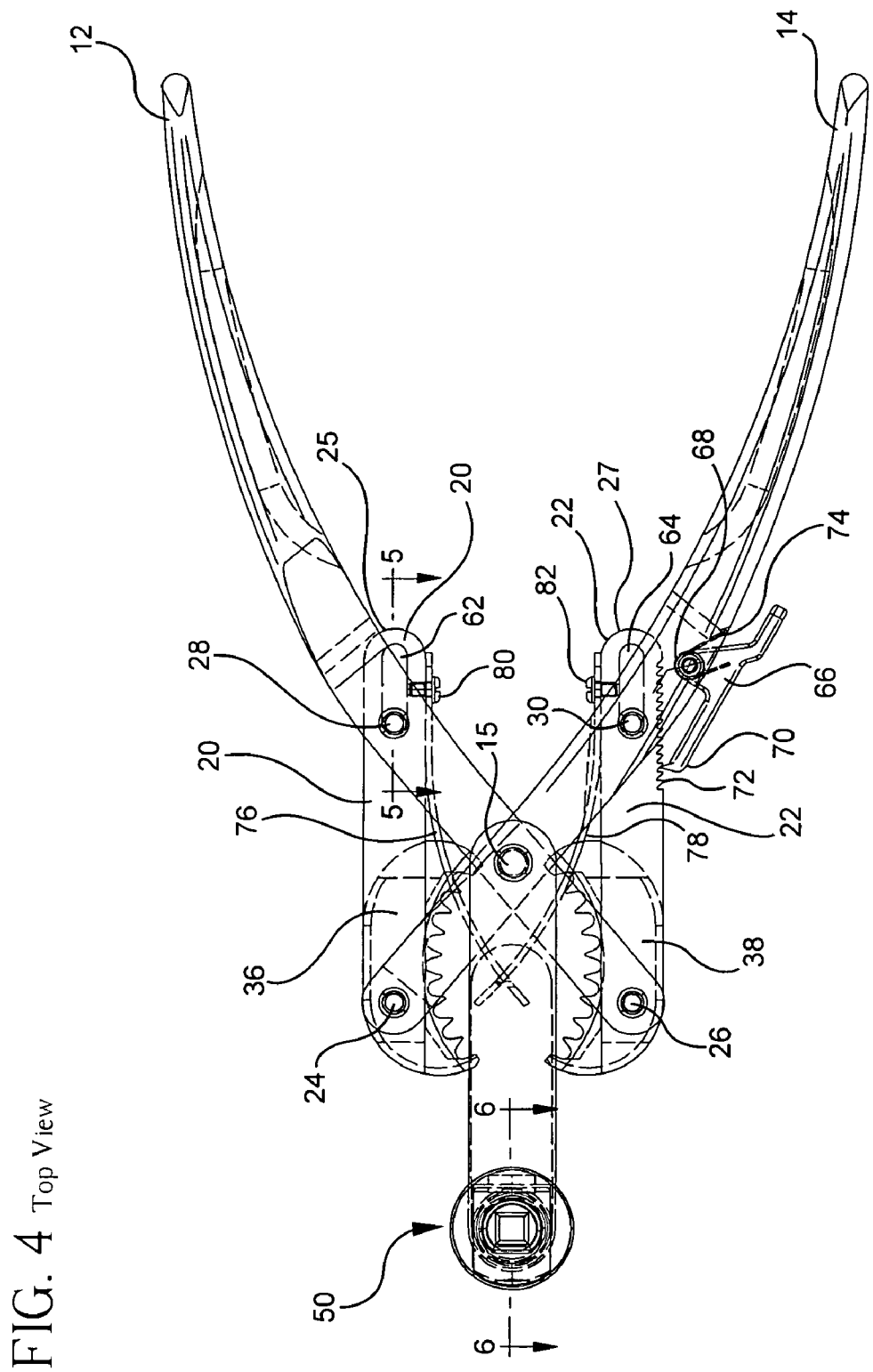
FIG. 4 Top View

PATELLA RESECTION CLAMP

BACKGROUND OF THE INVENTION

A patellar clamp and saw guide are used during a total knee arthroplasty procedure to prepare the posterior surface of a patellar bone to accept a prosthetic implant.

Typically, a surgeon will select a patellar prosthesis for implantation either by utilizing a resurfacing technique wherein the prosthetic patella will be resected and resurfaced or by an insetting procedure where the patella is inserted into the prepared surface of the patella. Accordingly, two varieties of guides could be available for connection to the patellar clamp and could be interchangeably connectable to the clamp. The interchangeable guides permit a surgeon to use the patellar clamp during either a total patellar bone resurfacing procedure or a patella insetting procedure.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

In either a total resurfacing procedure or a patella insetting procedure, it is important that a sufficient amount of bone stock remain after resection to accept the fixation pegs of the patellar prosthesis and maintain the integrity of the remaining patellar bone. Therefore, proper location of the saw blade is important. Furthermore, surgical techniques for implanting knee prosthesis have been developed whereby the bone surfaces are prepared and the implants are inserted through relatively small incisions made medially or laterally on the knee. Such a technique is shown in U.S. Publication No. 2003/0171757. In this technique, a patella cutting guide which does not require everting the patella and which permits a lateral or medial approach for resecting the patella.

Prior art devices for aiding the surgeon in performing patella resections are well known to those skilled in the art. For example, Peterson, in U.S. Pat. No. 4,663,862, teaches a method and instruments for the installation of a patella button prosthesis which involves performing a patella resection.

In particular, Peterson relates to a saw guide which comprises a pliers-like instrument having a pair of mutually pivotable jaw members. The jaw members are designed so as to enable them to surround the outer periphery of the patella with each jaw member having a respective handle, integrally formed therewith, which handles may be pivoted so as to pivot the jaw members to and from engagement with the patella periphery. At the ends of the handles, a locking device is provided which enables the locking of the jaw members about the patella periphery. The Peterson device requires that a flat saw blade be guided over the face of the jaw members after the patella has been set to the correct depth between the members.

U.S. Pat. No. 5,147,365 relates to a patella osteotomy guide in which the jaw members include a slot for guiding the flat saw blade and an arm for setting the saw blade depth in the patella.

U.S. Pat. No. 5,486,177 relates to a patella milling instrument having a clamp which contacts the underside of the patella. A similar clamping tool is shown in U.S. Pat. No. 5,284,482.

U.S. Pat. No. 5,222,955 relates to a reaming system designed to cut a conical bore in a patella surface while the patella is being held in a patella clamp similar to that disclosed in U.S. Pat. No. 5,284,482.

U.S. Pat. No. 5,941,884, the teachings of which are incorporated herein by reference, relates to a patella clamp which includes indicia of both the amount of bone resected and the amount of bone remaining. The resection depth is set via a stop collar on a toothed extension. U.S. Pat. No. 5,441,884 does not provide any method of setting the depth of the patella milling based on the amount of bone remaining. U.S. Pat. No. 5,575,793 is similar in that a gage is provided to set the amount of bone to be removed.

SUMMARY OF THE INVENTION

It is one aspect of the invention to provide an improved apparatus and method for facilitating the preparation of the natural patella to receive a patellar prosthesis.

It is an additional aspect of the invention to provide a clamping system which can hold the patella in position during resection without everting the patella.

It is yet another aspect of the invention to provide a patella resection instrument which can be used in a medial or lateral knee resection technique.

These and other aspects and advantages of the invention are provided by a patella resection clamp having first and second arms pivotally connected at a pivot point intermediate first and second ends of each arm. The first end of the first and second arms respectively having a first and second jaw portion and a second end of said arm having handle portions. The first and second jaw portions are offset in the direction of the pivot axis which, when in use, results in the first and second arm ends being displaced in the anterior/posterior direction. Each jaw portion has a first and second end defining a patella clamping surface therebetween. The jaw members have a saw blade guide slot with the first and second ends open into the slot. The open ends facing in a direction of the second end of the arms including the guide slot allowing medial, lateral or anterior-medial or anterior-lateral introduction of an oscillating saw blade when said jaws are clamped around the proximal-distal edges of the non-everted patella.

A method is also disclosed for resecting the posterior surface of the patella with an oscillating saw blade and comprises grasping a proximal surface of a non-everted patella with a first clamp and then grasping a distal surface of the non-everted patella with a second clamp. The first and second clamps are interconnected, preferably by a pivot pin, with at least one clamp moveable in a proximal-distal direction to clamp the patella therebetween. The clamps have medially and/or laterally facing saw blade slot so that a saw blade may be inserted through the guide slot or surface associated with the clamps in a medial/lateral direction and resection of the patella posterior surface is accomplished by advancing the saw blade in a medial/lateral direction. Preferably, the patella grasping surface is at a first end of each of the first and second clamps with a handle portion being located at a second end of each of the first and second clamps.

BRIEF DESCRIPTION OF THE DRAWINGS

The present invention will be better understood on reading the following detailed description of non-limiting embodiments thereof, and on examining the accompanying drawings, in which:

FIG. 4 is a top view of the patella clamp of FIG. 1;

DETAILED DESCRIPTION

Figure 1:
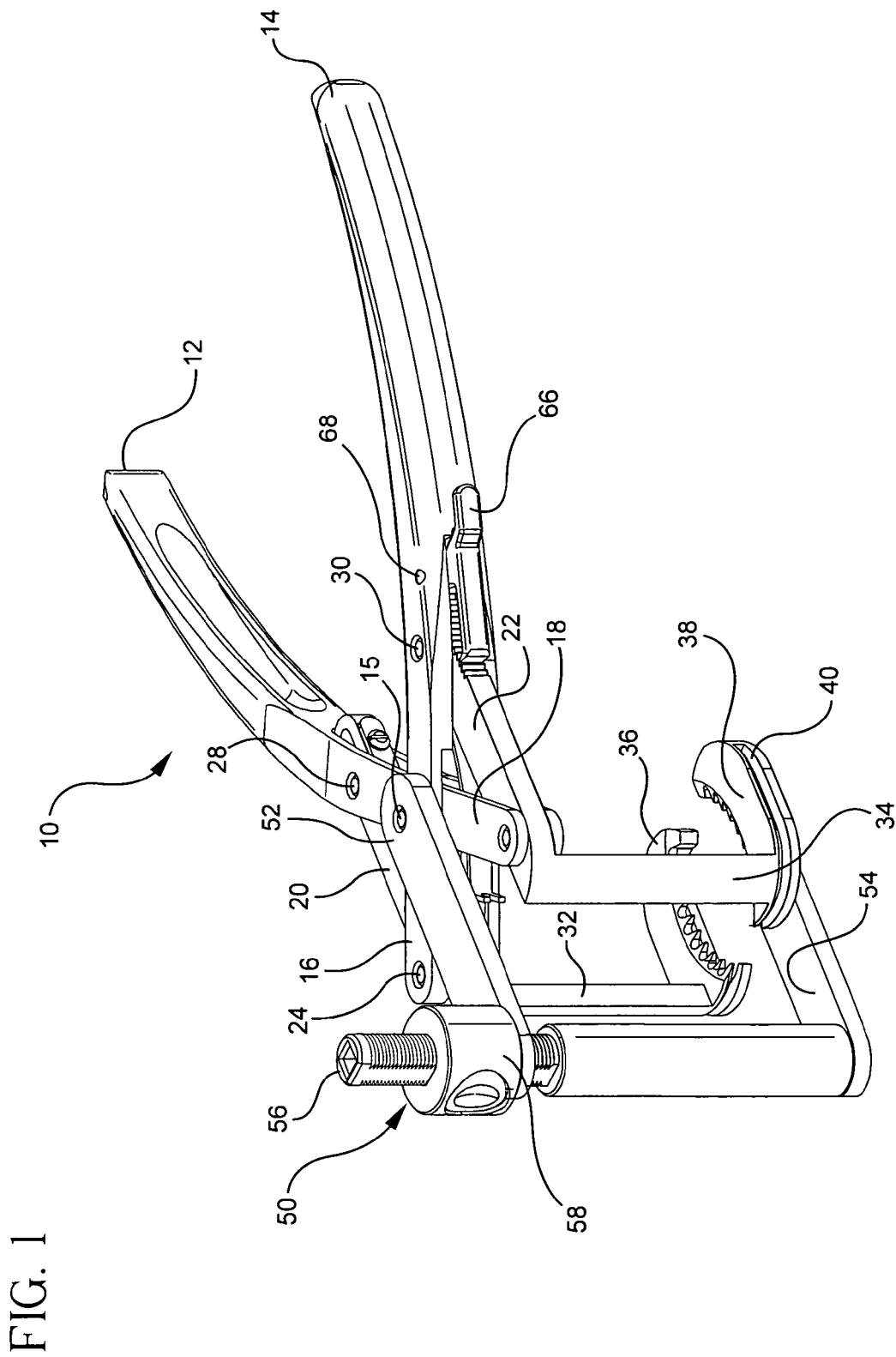
FIG. 1 is an isometric view of the patella clamp of the present invention.
Figure 2:
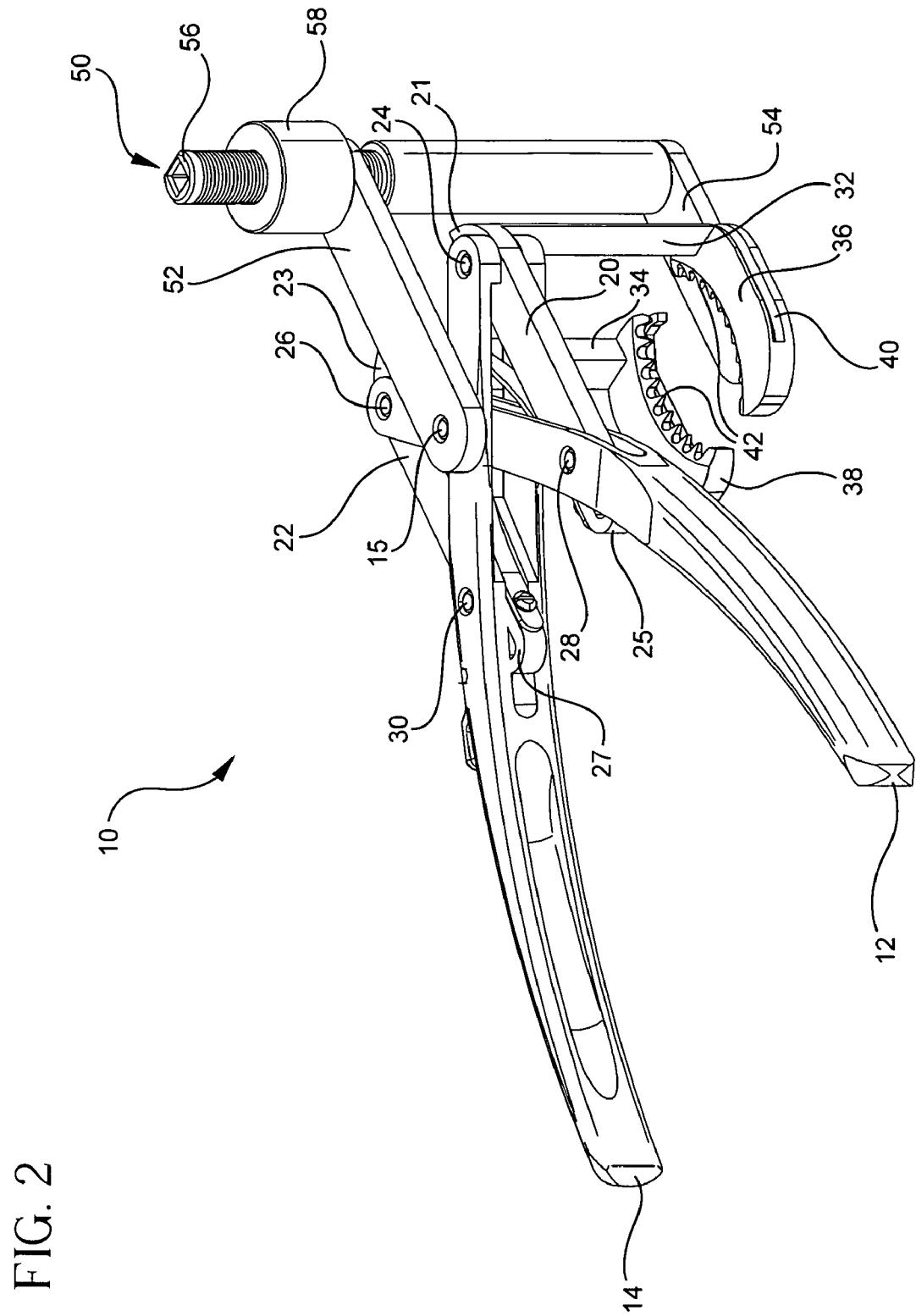
FIG. 2 is a rear perspective view of the patella clamp of FIG. 1.

Referring to FIGS. 1 and 2, there is shown the patella resection clamp of the present invention generally denoted as 10. Clamp 10 has two handle portions 12 and 14 having first ends 16 and 18 each coupled to respective clamp arms 20 and 22. Arms 12 and 14 extend in parallel direction and are generally coplanar.

Each handle portion 12 and 14 is pivotally connected to first ends 21, 23 of both arms 20 and 22 by pivot pins 24 and 26, respectively. Each handle portion 12 and 14 is also connected to second ends 25 and 27 of arms 20 and 22 at pivot points 28 and 30. As can be seen, each handle portion 12, 14 is coupled to both arms 20, 22. Handle portion 12 is coupled to arm 22 at pivot point 26 and arm 20 at pivot point 28. Likewise, handle portion 14 is connected to arm 20 at pivot point 24 and arm 22 at pivot point 30. Handle portions 12 and 14 are interconnected by a pivot pin 15 which pivotally couples the handle portions in a scissor-like manner. Arms 20 and 22, respectively, include downwardly extending legs 32 and 34 which, in the preferred embodiment, when mounted on the body, would extend posteriorly. Legs 32, 34 space the jaws 36, 38 posteriorly so that the entire handle part of the instrument can be spaced above (anteriorly) of the patient's knee joint.

In the preferred embodiment, each leg 32, 34 has one jaw element 36 and 38, respectively, extending in a medial-lateral direction therefrom. When mounted on the patella, jaws 36 and 38 extend in the medial-lateral direction being moved in a proximal-distal direction towards and away from one another.

In the preferred embodiment, jaws 36 and 38 include a saw blade guide slot or non-slotted guide surface 40 extending therethrough for accommodating and guiding a blade of an oscillating saw. Jaw elements 36 and 38 also include a plurality of teeth 42 for engaging the proximal and distal surfaces of the patella. The preferred clamp 10 includes a patella thickness gauge generally denoted as 50 which is mounted via an arm 52 mounted to an outwardly facing surface of handle 14 preferably at pivot pin 15. Arm 52 can be mounted in a modular manner so it can be removed from clamp 10 if desired. Resection level gauge 50 includes a patella contact arm 54 adapted to contact the posterior surface of the patella.

Contact arm 54 is coupled to a threaded shaft 56 which is connected to arm 52 via a threaded bushing 58. In the preferred embodiment, rotation of bushing 58 moves arm 56 in the anterior-posterior direction. Upon contacting the posterior surface of the patella with arm 54, post 56 may include markings, preferably in 1 millimeter increments, which show the amount of patella bone which will be removed from the patella. This amount is the distance between slot 40 and the contact surface of arm 54. If the amount of bone being removed is excessive or insufficient, the jaw elements 36 and 38 may be readjusted on the patella as will be discussed in more detail below.

Figure 3:
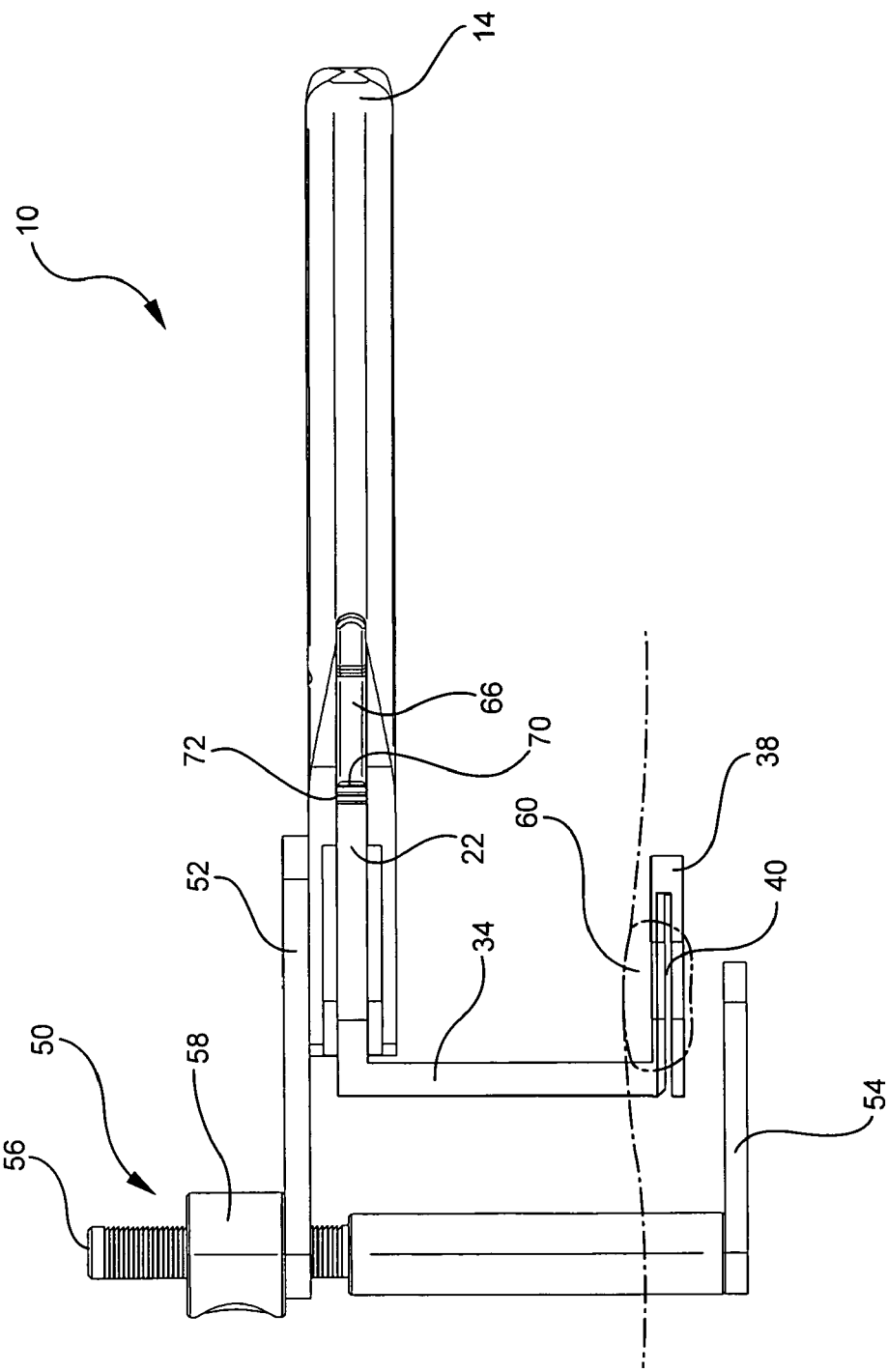
FIG. 3 is a side view of the patella clamps of FIGS. 1 and 2 showing a non-everted patella clamped between the jaws thereof.

Referring to FIG. 3, there is a side view showing patella resection clamp 10 of the present invention grasping a patella 60 with the contact arm 54 spaced posteriorly from the patella surface to be resected. As contacting arm 54 is moved upwardly in FIG. 3, it contacts the posterior surface of patella 60 with the distance between the upper surface of arm 54 and slot 40 defining the amount of bone to be removed.

Referring to FIG. 4, there is shown a top view of patella resection clamp 10 of FIGS. 1-3. From this view, it can be seen that the ends 25, 27 of arms 20 and 22 opposite jaw 36 and 38 are slotted with slots 62 and 64, respectively.

FIG. 4 also shows a locking mechanism which, in the preferred embodiment, includes a locking pawl 66 pivotally coupled to handle portion 14 by a pivot pin 68. Locking pawl 66 includes a tip 70 which engages a series of teeth 72 on the outer surface of arm 22. Pawl 66 is spring-biased by a spring 74, which acts around pivot point 68, to bias the tip 70 of pawl 66 into engagement with teeth 72 to thereby lock the jaws 36, 38 and arms 12, 14 in a selected position.

Arms 20 and 22 are spring-biased to the jaw open position by leaf-type springs 76 and 78. Springs 76 and 78 force jaws 36, 38 out of engagement with patella 60 and, as a consequence of the pivot connections 24, 26 and pins 28 and 30 sliding in slots 62 and 64, cause handle portions 12 and 14 to simultaneously move away from one another. Springs 76 and 78 are preferably attached to arms 20 and 22 adjacent their slotted ends by, in the preferred embodiment, screws 80 and 82. Preferably the springs are bent or curved inwardly towards the center line of the instrument so that the movement of handle portions 12 and 14 towards one another causes arms 20 and 22 to move towards one another in a manner which tends to straighten curved springs 76 and 78 causing the spring force to increase.

Figure 5:
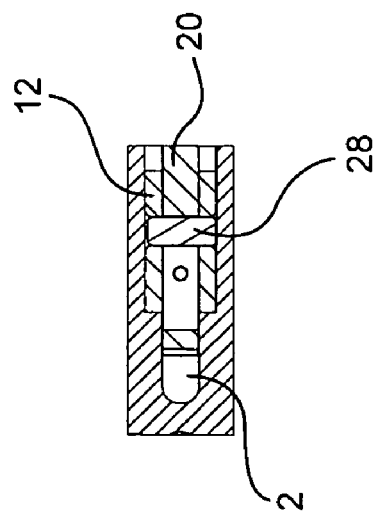
FIG. 5 is a cross-sectional view along lines 5-5 of FIG. 4.

Referring to FIG. 5, there is shown a cross-sectional view through the slotted portion of arm 20. While arm 20 is shown, the same structure is present on arm 22. The travel of pin 28 in slot 62 and of pin 30 in slot 64 delimits the maximum movement of jaws 36 and 38 towards and away from one another. Thus, when pins 28, 30 are located at the ends of slot 62, 64 towards jaw members 36 and 38, the jaws are in their closest position and when the pins 28, 30 are at opposite ends of the slots, the jaws are in their most open position.

Figure 6:
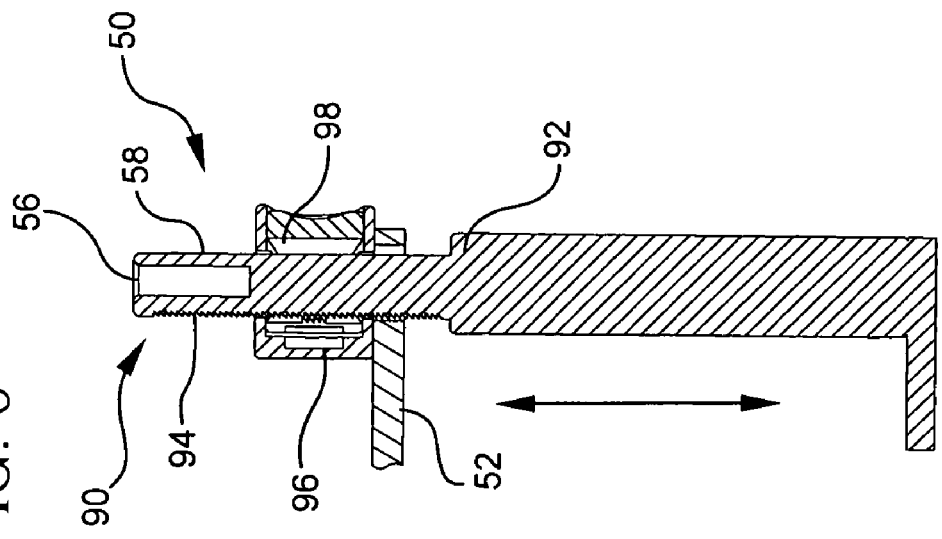
FIG. 6 is a sectional view along lines 6-6 of FIG. 4.
Figure 8:
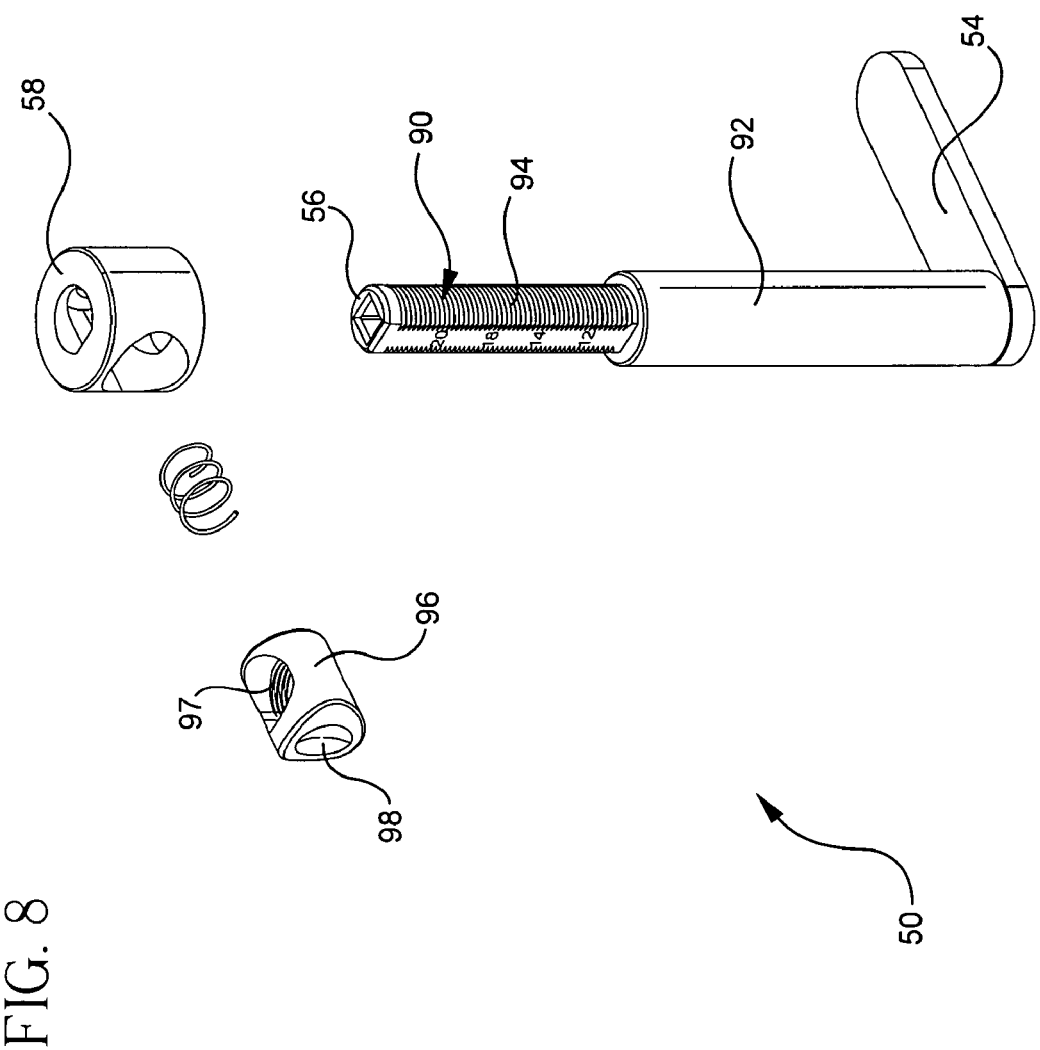
FIG. 8 is an exploded view of the patella thickness gauge of the clamp of the present invention.

Referring to FIGS. 6 and 8, there is shown a cross-sectional view (FIG. 6) and an exploded view (FIG. 8) of the patella measuring gauge 50. In the preferred embodiment, shaft 56 includes a threaded portion 90 and an unthreaded portion 92. It is possible to have the entire shaft 56 threaded. In the preferred embodiment, gauge arm 54 is made integral with portion 92 of shaft 56 and, in addition, thread portion 90 is mounted on arm 52 of the gauge assembly. In turn, arm 52 is, in the preferred embodiment, pivotally connected to pivot pin 15 which pivotally connects handle portions 12 and 14. In the preferred embodiment, bushing 58 includes a releasable portion 96 having threads 97 which engage the threads 94 of portion 90. Portion 96 is preferably in the form of a spring loaded pawl element which is spring-biased into engagement with teeth 94 and may be released from engagement of threads 94 by depressing button 98, which moves teeth 97 of pawl 96 out of engagement with teeth 94 against the force of the spring. Since bushing 58 is fixed to arm 52, release of pawl 96 allows shaft 56 to move up and down as depicted in FIG. 6 (in the anterior-posterior direction when fixed to a patella) to thereby enable contact arm 54 to engage the posterior surface of patella 60. In the preferred embodiment the contact arm assembly 54, 56 can be completely removed from the arm 52 by the release of pawl 96.

Figure 7:
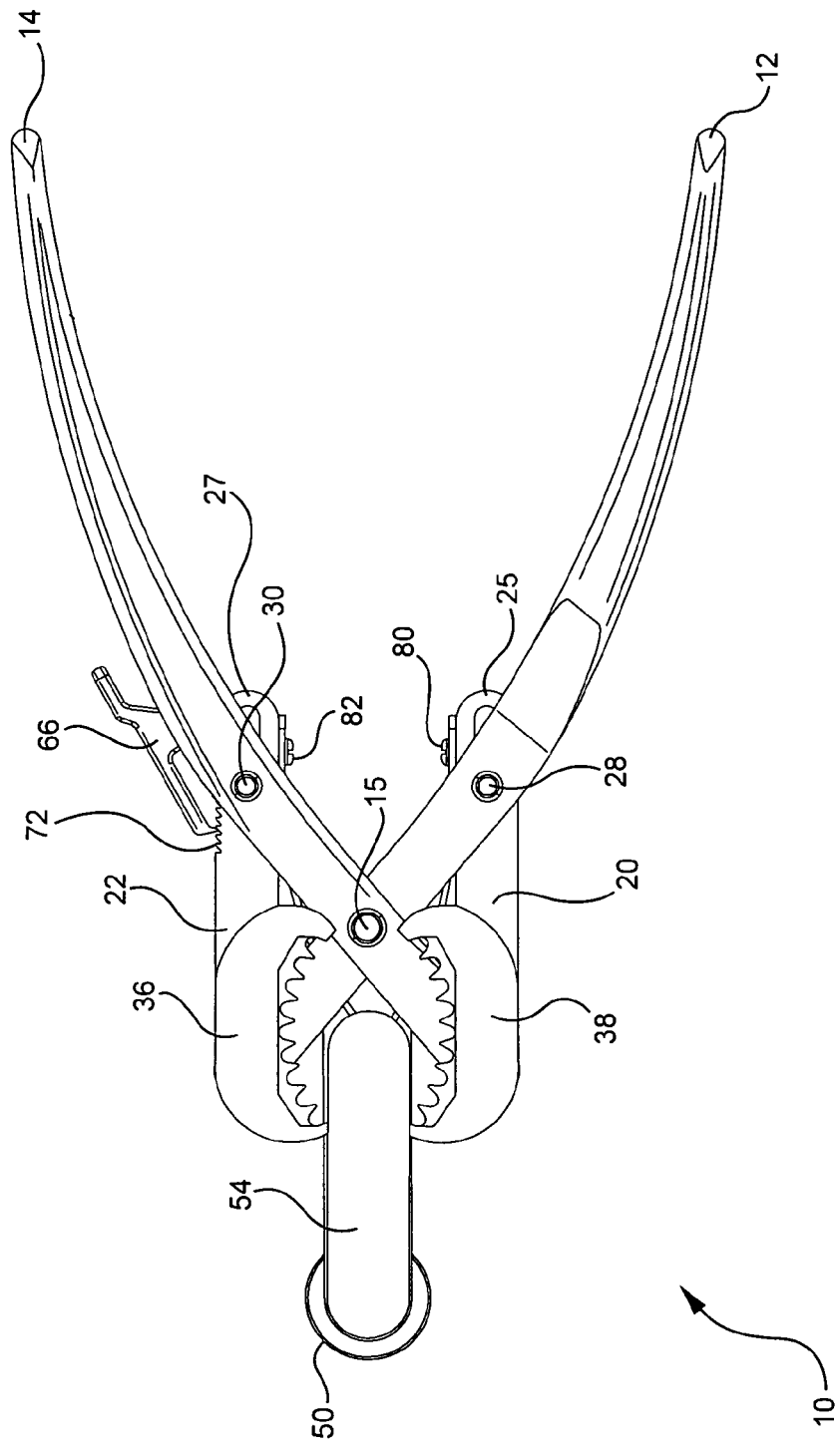
FIG. 7 is a bottom view of the patella resection clamp of the present invention.

Referring to FIG. 7, there is shown a bottom view of the patella resection clamp of the present invention, including the patella gauge 50 and the bottom or posterior surface of arm 54. The elements of FIG. 6 have been numbered corresponding to the various elements described above.

Figure 9:
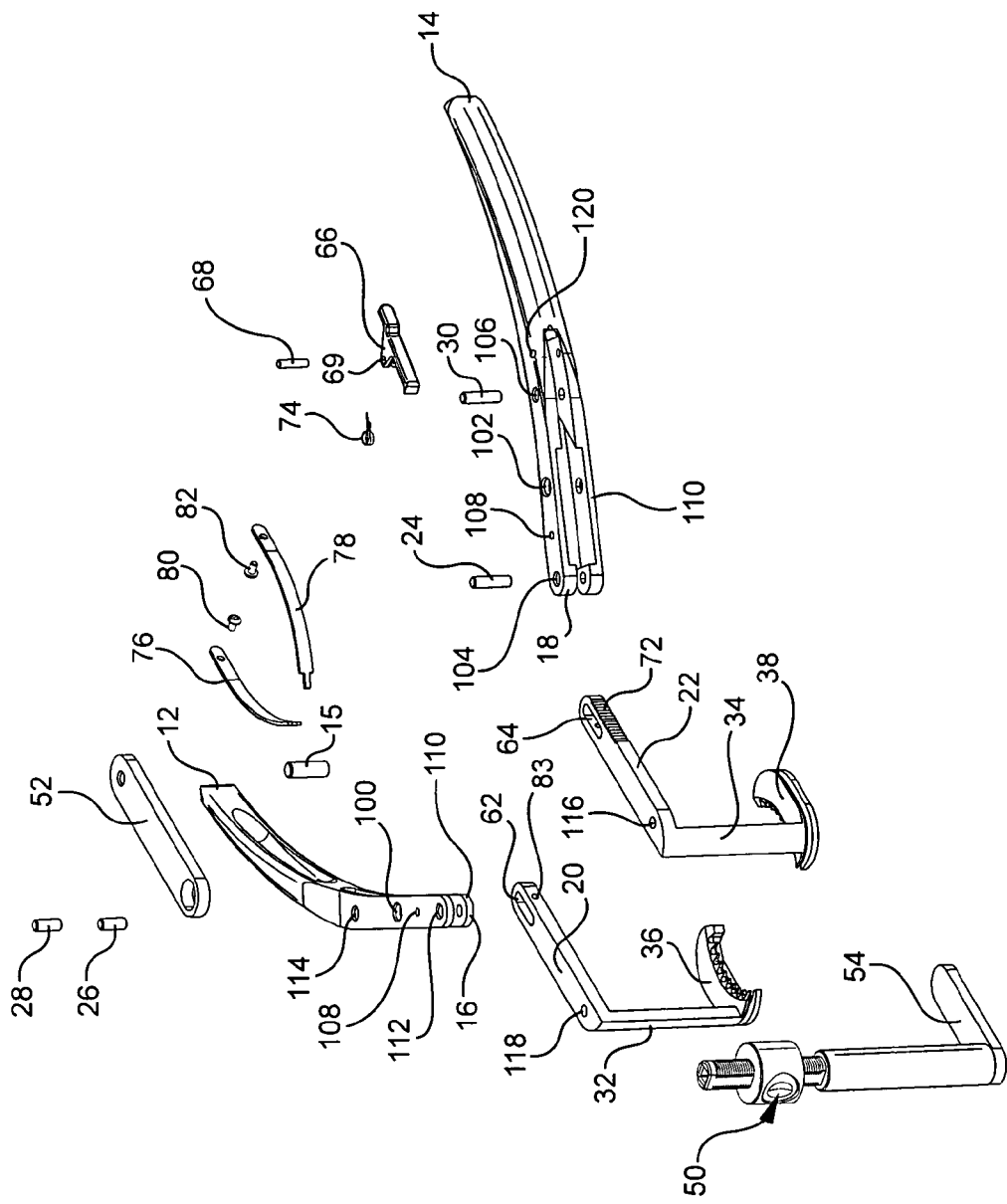
FIG. 9 is an exploded view of the patella clamp of FIG. 1.

Referring to FIG. 9, there is shown an exploded view of the patella resection clamp 10 including the parts discussed above. For example, handle portions 12 and 14 would be joined by pivot pin 15 located in bores 100 and 102 of portions 12 and 14 respectively. Likewise, with regard to handle portion 14, pivot pins 24 and 30 are inserted through bores 104, 106 in handle portion 14. In the preferred embodiment, end portions 16 and 18 of handle portion 12 and 14 have bifurcated upper and lower portions 108 and 110, respectively, for receiving arms 20 and 22 of jaw members 36 and 38. Handle portion 12 includes pivot pins 26 and 28 which are inserted through bores 112 and 114 of handle portion 12 with pin 28 engaging slot 62 and pin 26 engaging in bore 116 of arm 22. Likewise, pin 24 extends through bore 104 of arm 14 into bore 118 of arm 20 and pin 30 engages slot 64 of arm 22. FIG. 9 also shows pawl 66 including spring 74 which surrounds pivot pin 68 which is inserted through bore 69 in pawl 66 and bores 120 in the bifurcated section of handle portion 14. Springs 76 and 78 and associated screws 80 and 82 are also shown disassembled from handle portions 12 and 14. For example, screw 80 engages threaded bore 83 in arm 20.

Figure 10:
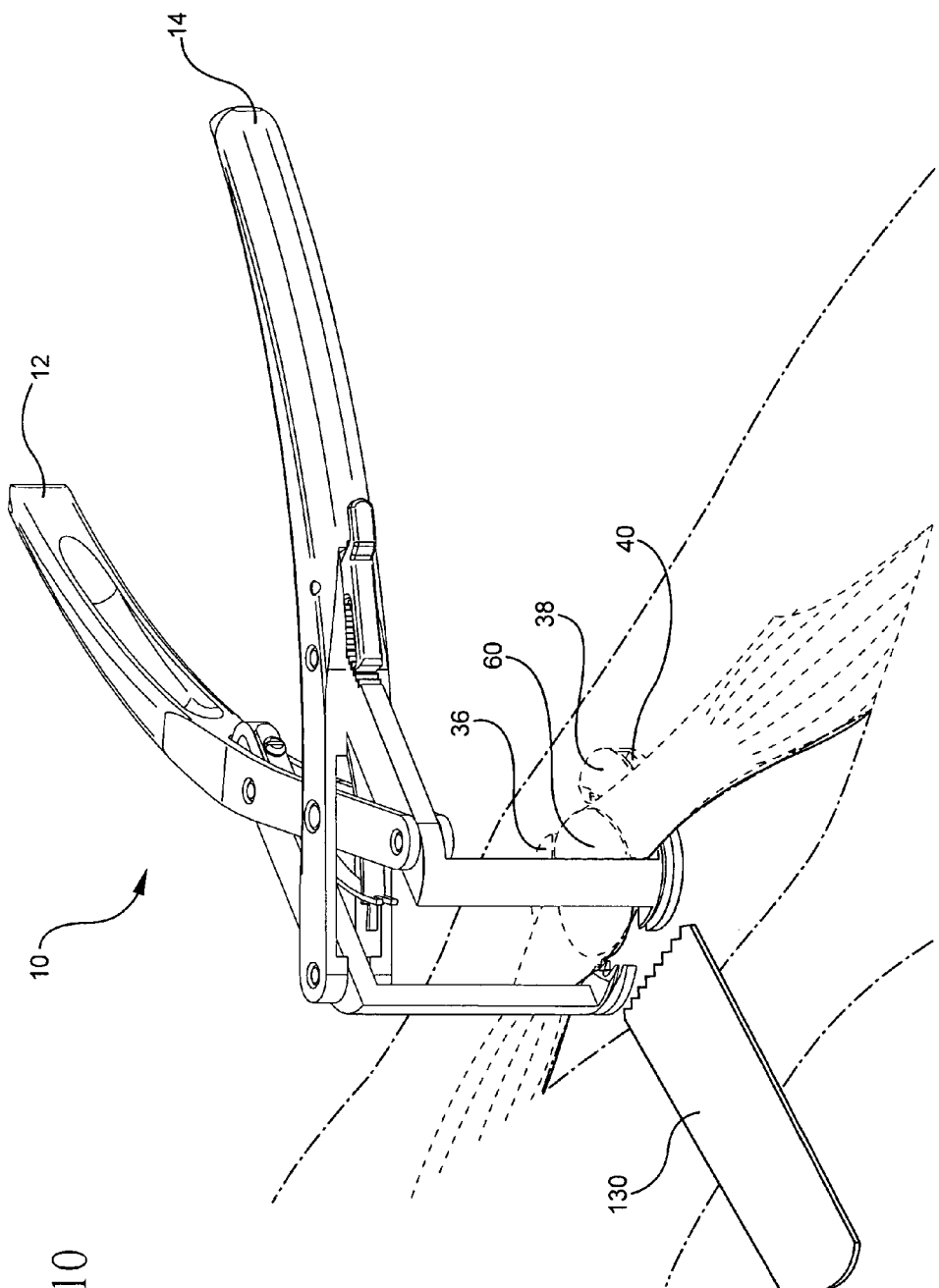
FIG. 10 is a perspective view of the patella resection clamp of the present invention engaging the patella and a saw blade used for patella resection.
Figure 11:
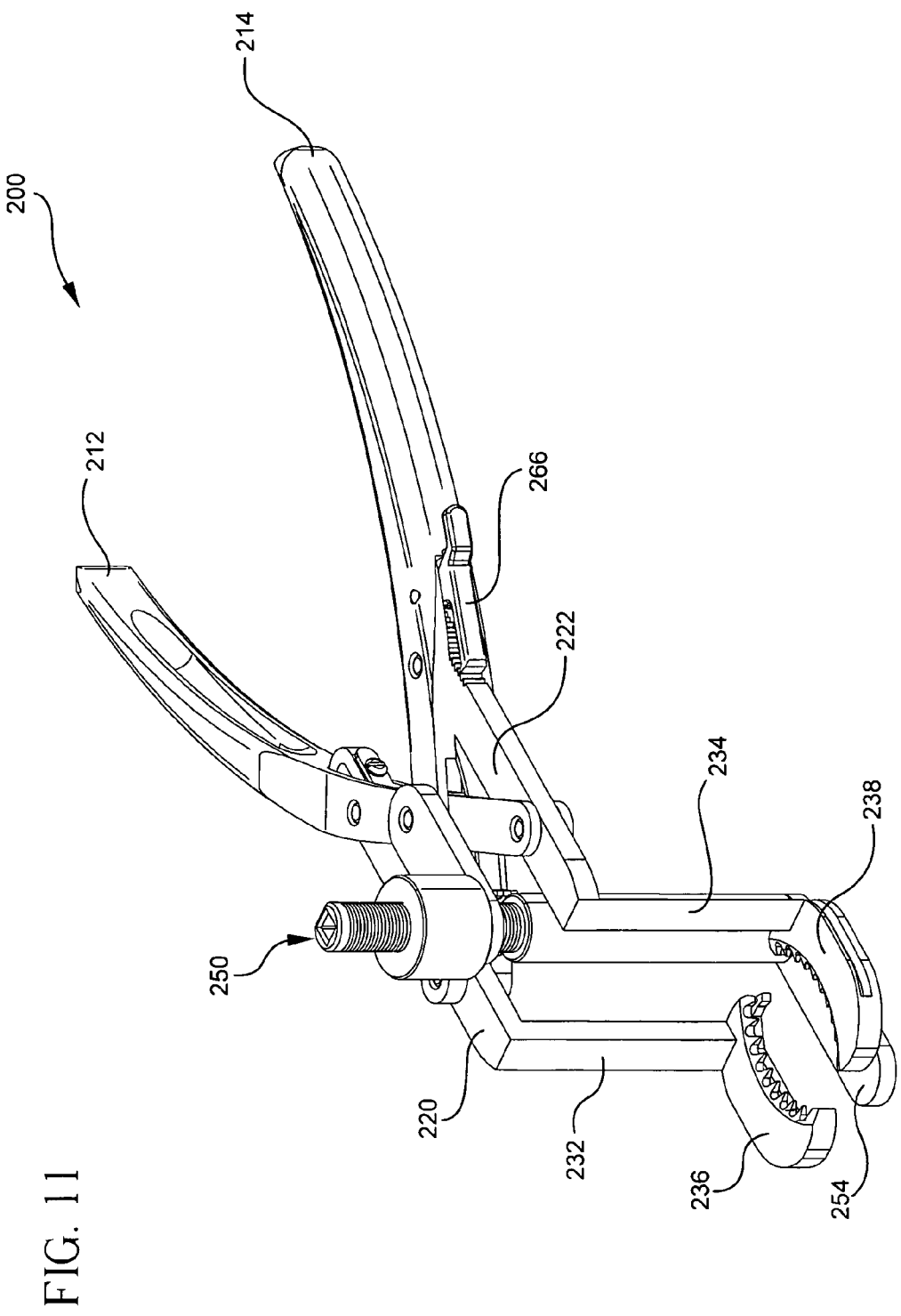
FIG. 11 is a perspective view of a second embodiment of the patella resection clamp of the present invention.
Figure 12:
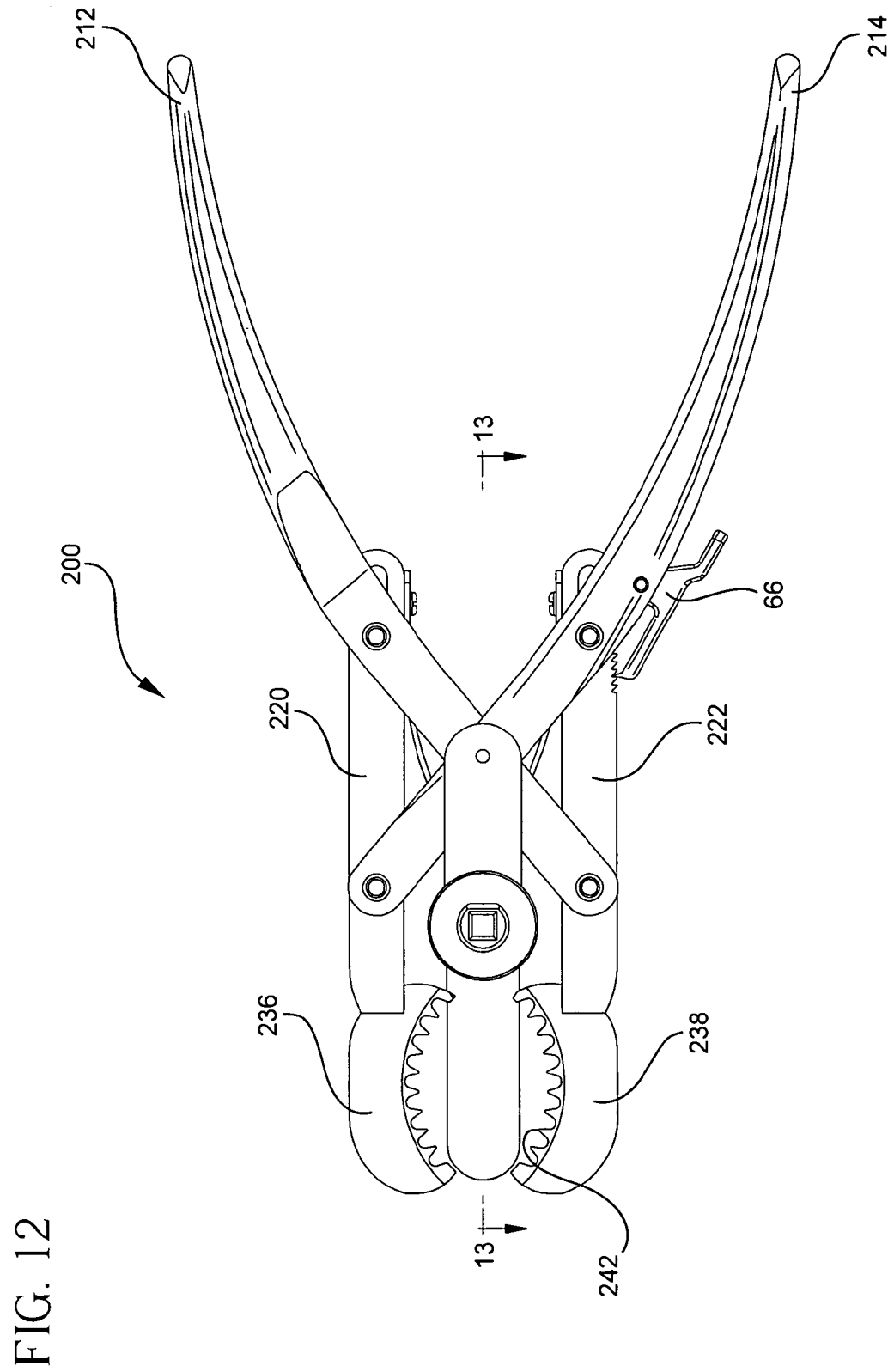
FIG. 12 is a bottom view of the patella resection clamp of FIG. 11.

Referring to FIG. 10, there is shown a lateral approach to a left leg and a patella resection clamp 10 mounted on patella 60 with the jaw members 36 and 38 oriented in a medial-lateral direction. An oscillating saw 130 is shown extending into a laterally facing open portion of slot or guide surface 40 for cutting the posterior surface of patella 60. Only the lateral side of the patella need be exposed with the medial side remaining under the incision. Note that the measuring assembly 50 has been removed from the patella resection clamp for this operation. Alternately, it could be left on and swung out of the way.

Referring to FIGS. 11-14, there is shown a second embodiment of the patella resection clamp of the present invention generally denoted as 200. This embodiment is almost identical to the patella resection clamp 10 previously described with the exception that jaw members 236 and 238 extend in a direction away from handle portions 212 and 214 rather than towards handle portions 12 and 14 as shown in the figures depicting patella resection clamp 10. Likewise, removable patella thickness gauge 250 includes a contact arm 54 which extends away from handle portions 212, 214 rather than towards handle portions 12 and 14 as in the preferred embodiment 10. Jaws 236 and 238 are again spaced posteriorly by posts 232 and 234 so that the handle portion of the instrument will be anterior to the knee joint during use. Patella resection clamp 200 is, in all other respects, identical to that previously described, including a locking pawl 266 and the spring mechanisms biasing the handle portions to the open position as previously described.

Figure 13:
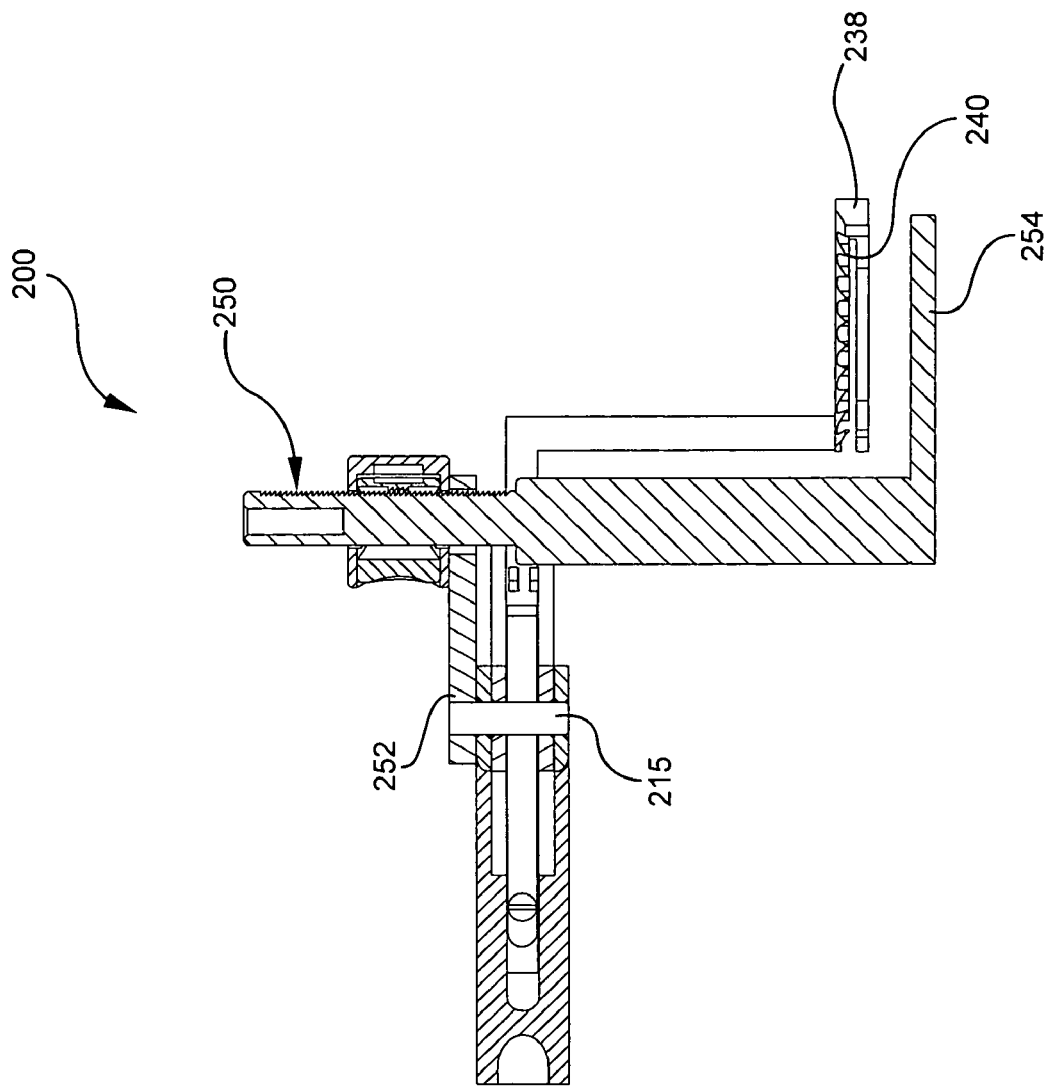
FIG. 13 is a cross-sectional view taken along lines 13-13 of FIG. 12.
Figure 14:
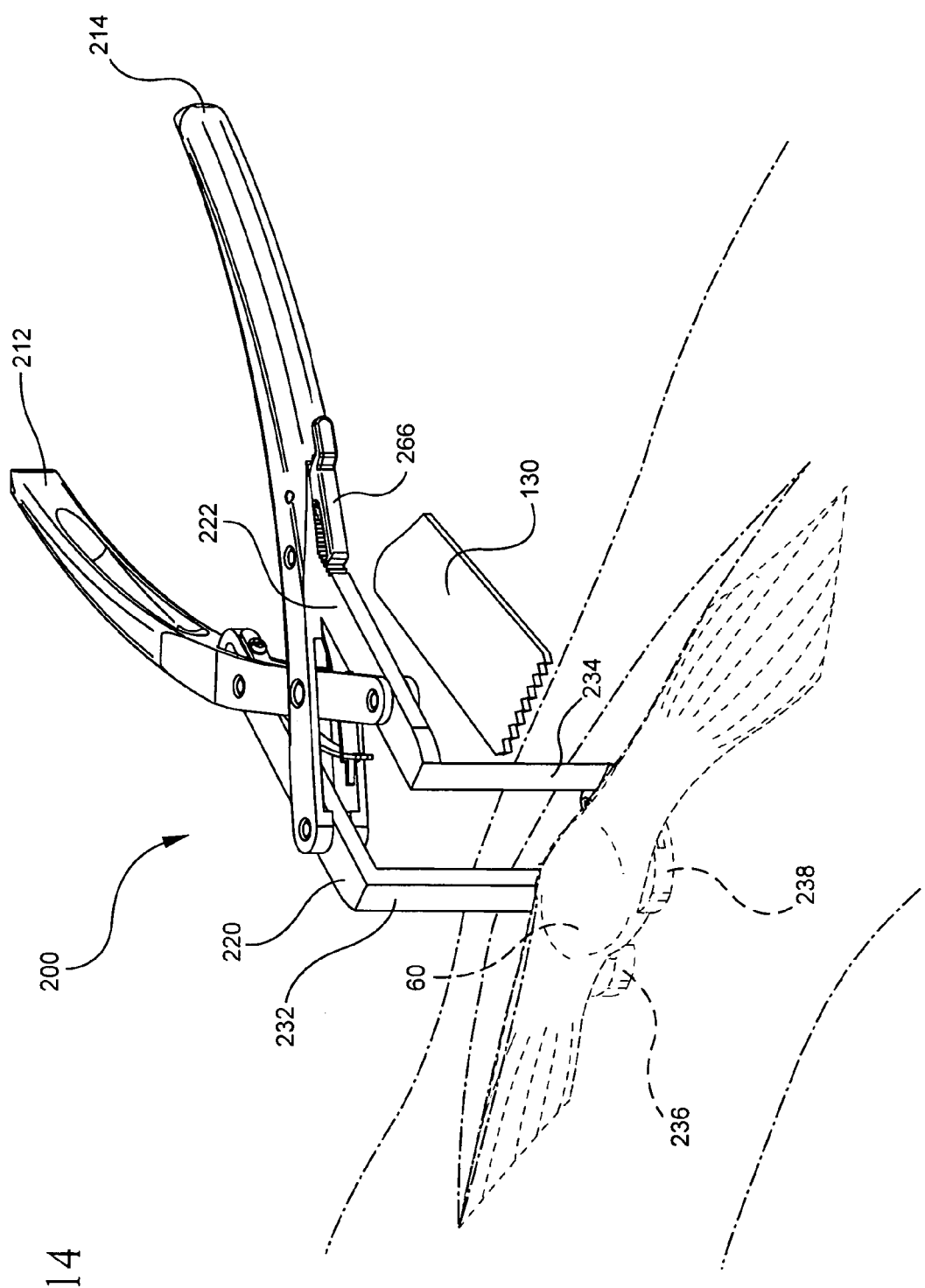
FIG. 14 is a perspective view of the second embodiment of the patella resection clamp of the present invention engaging the patella and a saw blade used for patella resection.

Referring to FIG. 13, there is shown a cross-sectional view of the second embodiment 200 which clearly shows the jaw portion 238 including saw blade slot 240 and teeth 242 with gauge 250 removably mounted on pivot pin 215 with contact arm 54 oriented in a direction away from handles 212, 214. The release and movement of arm 254 is done in the same manner as arm 54. FIG. 14 is similar to FIG. 10 but shows the use of the second embodiment of the resection clamp in a medical approach to the left leg.

The preferred use of the patella clamp 10, 200 will now be described. Preferably, an incision is made on either the lateral or medial side of the patella and the jaw members 36 and 38 are inserted into the incision and clamped on the periphery of the patella without everting the patella. Preferably the proximal and distal patella surfaces are engaged. The embodiment of the patella clamp 10 is best suited for use when as assistant holds the handles of the clamp while standing on one side of the patient's leg and the surgeon stands on the opposite side and performs the bone cut in-situ. Alternatively, the patella clamp 200 is best suited when the surgeon holds the patella clamp handles and performs the bone resection. In this manner, the saw blade passes under the clamp handles to make the cut in-situ. It should be noted that the jaw portions 32, 34 and 232, 234 can be made modular for ease of switching to an approach preferred by the surgeon.

In either case, once the jaws are clamped around the proximal and distal surfaces of a non-everted patella 60 by moving handles 12, 14 towards one another. The patella thickness gauge 50 is utilized to measure the amount of bone to be removed. This is done by adjusting contact arm 54 into contact with the posterior surface of patella 60. Markings, best shown on FIG. 8 on gauge 50 will indicate the amount of bone to be removed from the patella, i.e. the distance from the top of gauge arm 54 to the tope of slot 40. This distance can be adjusted by repositioning the jaws on the patella using button 98. Alternately, the position of arm 54 for a desired thickness can be set initially and the jaws 36, 38 clamped onto the patella with the top of contact arm 54 engaging the posterior surface of the patella. Once the correct depth is set, the gauge 50 is preferably removed from the patella resection clamp. An oscillating saw blade is then placed through slots or on a guide surface 40 either from a purely lateral or from a proximal-lateral or distal-lateral direction and the patella surface is resected. Alternately, the blade can be inserted into the slot from the medial side. Once the resection is complete, the assembly is removed from the remaining patella. The blade is always inserted in the direction of an axis extending perpendicular to the pivot axis between handles 12, 14 and between jaw members 36, 38, 236, 238. Thus the surgeon can move the saw blade 130 in a direction below but parallel to the handles 12, 14 of the resection clamp 10 and advance the blade in a direction perpendicular the clamping direction of the jaws. The patella is then resurfaced in the standard manner, for example, with a polyethylene bearing.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A patella resection clamp for use in resecting a patella comprising:

a first elongated portion and a second elongated portion, each of said portions having first and second ends, said portions pivotally connected at a pivot point intermediate said first and second ends for rotation about a pivot axis, the second end of each of said elongated portions including a jaw, said jaw of said first and second portions spaced from said second end of said elongated portions in a direction parallel to said pivot axis, each of said jaws of said first and second elongated portions having first and second ends, said jaws spaced to form an opening therebetween for receiving the proximal and distal edges of the patella, said jaw portions including a saw blade guide surface open to at least one of said first or second ends of each of said jaw portions for receiving a saw blade extending in a direction generally aligned with a axis perpendicular to said pivot axis extending between said jaws of said first and second elongated portions, wherein each of said first and second jaw portions includes first and second L-shaped brackets with a first end of a leg of each of said L-shaped brackets fixedly attached to each of said jaws, said legs extending in a direction parallel to a pivot axis through said pivot point and an arm of each of said L-shaped brackets pivotally coupled to said first and second elongated portions respectively.

2. The patella resection clamp as set forth in claim 1 wherein said leg of each of said L-shaped brackets extends from a first end of each of said jaw portions to a first end of each of said arms.

3. The patella clamp as set forth in claim 2 wherein second ends of said arms of each of said first and second L-shaped brackets include a slot in which a pivot pin fixedly coupled to said respective first and second elongated portions can slide as said first and second elongated portions pivot about said pivot point.

4. The patella resection clamp as set forth in claim 3 wherein an arm of said first and second brackets includes a locking mechanism for engaging a respective one of said elongated portions to prevent the pivoting of said first and second elongated portions about said pivot point therebetween.

5. The patella resection clamp as set forth in claim 4 wherein the second ends of said first and second arms are handle portions and are spring biased away from one another.

6. The patella resection clamp as set forth in claim 1 wherein between the first and second ends of each of said jaws are patella engaging teeth.

7. The patella resection clamp as set forth in claim 1 further comprising a stylus for contacting an exposed posterior surface of said patella.

8. The patella resection clamp as set forth in claim 7 wherein said stylus is a U-shaped bracket mounted to a pivot pin pivotally connecting said first and second elongated portions.

9. The patella resection clamp as set forth in claim 8 wherein said U-shaped stylus includes a first portion coupled to said pivot point, a second portion extending from said first portion in a direction parallel to said pivot axis a distance greater than said leg of said jaws and a third bone contacting portion extending from said second stylus portion in a direction generally parallel to said first portion of said stylus.

10. The patella resection clamp as set forth in claim 7 wherein said stylus is an L-shaped bracket pivotally mounted on an arm coupled to said pivot pin.

11. The patella resection clamp as set forth in claim 10 wherein said L-shaped bracket of said stylus includes a first leg pivotally coupled to said arm and extending in a direction parallel to said pivot axis a distance greater than said jaw portions and a second leg having a bone contacting portion for engaging a posterior surface of the patella.

12. The patella resection instrument as set forth in claim 1 wherein said second end of said first and second elongated portions includes a handle portion.

13. A patella resection instrument for use resecting a posterior surface of a patella with a saw blade comprising:

a first handle portion having a patella engaging portion at a first end for engaging a proximal surface of the patella;

a second handle portion having a patella engaging portion at a first end for engaging a distal surface of the patella, said second handle portion pivotally coupled to said first handle portion for rotation about a pivot axis, said patella engaging portion of said first and second handle portions spaced from a second ends of said first and second handle portions along said pivot axis, said patella engaging portion of said first and second handle portions having a saw blade receiving guide surface open in a direction for receiving a saw blade inserted therein in a direction perpendicular to said pivot axis and between said patella engaging portions when said proximal and distal patellar surfaces are engaged by said patella engaging portion wherein each of said patella engaging portions of said first and second handle portions includes L-shaped mounting brackets with a first end of a leg of each of said L-shaped brackets attached to each of said jaw portions and extending in a direction parallel to said pivot axis and a first end of a an arm coupled to said leg of each of said L-shaped brackets pivotally coupled to one of said first and second handle portions at a first pivot point adjacent the first end of said handle portions and second ends of said arms pivotally coupled to the other of said first and second handle portion at a second pivot point on each handle portion spaced towards said handle portion second end.

14. The patella resection instrument as set forth in claim 13 wherein said second end of said handle portion includes a hand engaging portion.

15. The patella resection clamp as set forth in claim 13 wherein said leg of each of said L-shaped brackets extends from the first end of each of saw patella engaging portions.

16. The patella clamp as set forth in claim 15 wherein said second ends of said arms of each of said brackets include a slot in which a pivot pin fixedly coupled to said respective first and second handle portion can slide as said first and second handle portions pivot about said second pivot point.

17. The patella resection clamp as set forth in claim 16 wherein one of said bracket arms includes a locking mechanism for engaging a respective one of said handle portion to selectively prevent the pivoting of said bracket with respect to said handle portion.

18. The patella resection clamp as set forth in claim 13 wherein the second ends of said first and second handle portion are spring biased away from one another.

19. The patella resection clamp as set forth in claim 13 wherein the patella engaging portion of the first ends of each of said first and second handle portions include patella engaging teeth.

20. The patella resection clamp as set forth in claim 13 further comprising a stylus for contacting a posterior surface of the patella.

21. The patella resection clamp as set forth in claim 20 wherein said stylus is a U-shaped bracket pivotally mounted to a pivot pin pivotally connecting said first and second handle portions at said pivot axis.

22. The patella resection clamp as set forth in claim 21 wherein said U-shaped stylus includes a first portion coupled to said pivot point and extending towards said patella engaging portions, a second portion coupled to said first portion and extending in a direction parallel to said pivot axis a distance greater than said patella engaging portions and a third bone contacting portion extending from said second stylus portion towards an end of said handle portions.

23. The patella resection instrument as set forth in claim 20 wherein said stylus is an L-shaped bracket mounted on an extension coupled to a pivot pin at said pivot axis between said first and second arms.

24. The patella resection instrument as set forth in claim 23 wherein said L-shaped bracket includes a first leg pivotally coupled to said extension and extending in a direction parallel to said pivot axis a distance greater than said jaw portions and a second leg having a bone contacting portion for engaging a posterior surface of the patella.

25. The patella resection instrument as set forth in claim 24 wherein said first leg is moveable with respect to said extension in a direction parallel to said pivot axis.

26. The patella resection instrument as set forth in claim 25 wherein said first leg includes depth markings.

27. The patella resection instrument as set forth in claim 13 wherein said patella engaging portion of said first and second handles extends from the first ends of said handles towards a second end of said handles.

28. The patella resection instrument as set forth in claim 13 wherein said patella engaging portion of said first and second handles extends in a direction away from the first ends of said handles.

29. A patella resection clamp for use in resecting a patella comprising:

a first elongated portion and a second elongated portion, each of said portions having first and second ends, said portions pivotally connected at a pivot point intermediate said first and second ends for rotation about a pivot axis, the second end of each of said elongated portions including a jaw, said jaw of said first and second portions spaced from said second end of said elongated portions in a direction parallel to said pivot axis by a leg, each of said jaws of said first and second elongated portions having first and second ends, said jaws spaced to form an opening therebetween for receiving the proximal and distal edges of the patella, said jaw portions including a saw blade guide surface open to at least one of said first or second ends of each of said jaw portions for receiving a saw blade extending in a direction generally aligned with a axis perpendicular to said pivot axis extending between said jaws of said first and second elongated portions, further comprising a stylus for contacting an exposed posterior surface of said patella, wherein said stylus is a U-shaped bracket mounted to a pivot pin pivotally connecting said first and second elongated portions and wherein said U-shaped stylus includes a first portion coupled to said pivot point, a second portion extending from said first portion in a direction parallel to said pivot axis a distance greater than said leg of said jaws and a third bone contacting portion extending from said second stylus portion in a direction generally parallel to said first portion of said stylus.

30. A patella resection clamp for use in resecting a patella comprising:

a first elongated portion and a second elongated portion, each of said portions having first and second ends, said portions pivotally connected at a pivot point intermediate said first and second ends for rotation about a pivot axis, the second end of each of said elongated portions including a jaw, said jaw of said first and second portions spaced from said second end of said elongated portions in a direction parallel to said pivot axis, each of said jaws of said first and second elongated portions having first and second ends, said jaws spaced to form an opening therebetween for receiving the proximal and distal edges of the patella, said jaw portions including a saw blade guide surface open to at least one of said first or second ends of each of said jaw portions for receiving a saw blade extending in a direction generally aligned with a axis perpendicular to said pivot axis extending between said jaws of said first and second elongated portions, further comprising a stylus for contacting an exposed posterior surface of said patella, wherein said stylus is an L-shaped bracket pivotally mounted on an arm coupled to a pivot pin pivotally connecting said first and second elongated portions and wherein said L-shaped bracket of said stylus includes a first leg pivotally coupled to said arm and extending in a direction parallel to said pivot axis a distance greater than said jaw portions and a second leg having a bone contacting portion for engaging a posterior surface of the patella.

31. A patella resection instrument for use in resecting a posterior surface of a patella with a saw blade comprising:

a first handle portion having a patella engaging portion at a first end for engaging a proximal surface of the patella;
a second handle portion having a patella engaging portion at a first end for engaging a distal surface of the patella, said second handle portion pivotally coupled to said first handle portion for rotation about a pivot axis, said patella engaging portion of said first and second handle portions spaced from second ends of said first and second handle portions along said pivot axis, said patella engaging portion of said first and second handle portions having a saw blade receiving guide surface open in a direction for receiving a saw blade inserted therein in a direction perpendicular to said pivot axis and between said patella engaging portions when said proximal and distal patellar surfaces are engaged by said patella engaging portions, further comprising a stylus for contacting a posterior surface of the patella, wherein said stylus is a U-shaped bracket pivotally mounted to a pivot pin pivotally connecting said first and second handle portions at said pivot axis, wherein said U-shaped stylus includes a first portion coupled to said pivot pin and extending towards said patella engaging portions, a second portion coupled to said first portion and extending in a direction parallel to said pivot axis a distance greater than said patella engaging portions and a third bone contacting portion extending from said second stylus portion towards an end of said handle portions.

32. A patella resection instrument for use resecting a posterior surface of a patella with a saw blade comprising:

a first handle portion having a patella engaging portion at a first end for engaging a proximal surface of the patella;
a second handle portion having a patella engaging portion at a first end for engaging a distal surface of the patella, said second handle portion pivotally coupled to said first handle portion for rotation about a pivot axis, said patella engaging portion of said first and second handle portions spaced from second ends of said first and second handle portions along said pivot axis, said patella engaging portion of said first and second handle portions having a saw blade receiving guide surface open in a direction for receiving a saw blade inserted therein in a direction perpendicular to said pivot axis and between said patella engaging portions when said proximal and distal patellar surfaces are engaged by said patella engaging portion further comprising a stylus for contacting a posterior surface of the patella wherein said stylus is an L-shaped bracket mounted on an extension coupled to a pivot pin at said pivot axis between said first and second arms wherein said L-shaped bracket includes a first leg pivotally coupled to said extension and extending in a direction parallel to said pivot axis a distance greater than said jaw portions and a second leg having a bone contacting portion for engaging a posterior surface of the patella.

* * * * *